(12) United States Patent
Chen et al.

(10) Patent No.: US 6,433,178 B2
(45) Date of Patent: Aug. 13, 2002

(54) 3-ALKYL-3-PHENYL-PIPERIDINES

(75) Inventors: Michael Huai Gu Chen; Fu-Zon Chung; Helen Tsenwhei Lee, all of Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/873,889

(22) Filed: Jun. 4, 2001

Related U.S. Application Data

(60) Continuation of application No. 09/467,431, filed on Dec. 20, 1999, now abandoned, which is a division of application No. 08/983,584, filed as application No. PCT/US97/15443 on Sep. 2, 1997, now Pat. No. 6,040,316.
(60) Provisional application No. 60/026,385, filed on Sep. 16, 1996.

(51) Int. Cl.⁷ .................... C07D 401/06; A61K 31/445; A01P 25/24
(52) U.S. Cl. .................... 546/187; 546/191; 514/316
(58) Field of Search ................ 546/187, 191; 514/316

(56) References Cited

U.S. PATENT DOCUMENTS 5,340,822 A * 8/1994 Emonds-Alt et al. ....... 540/524
5,741,910 A * 4/1998 Bichon et al. ............. 546/224

FOREIGN PATENT DOCUMENTS

EP     0 714 891 A1 * 11/1995

\* cited by examiner

*Primary Examiner*—Richard L. Raymond
*Assistant Examiner*—Venkataraman Balasubramanian
(74) *Attorney, Agent, or Firm*—David R. Kurlandsky; Heidi M. Bervan

(57) ABSTRACT

The small nonpeptides of the instant invention are tachykinin antagonists. The compounds are highly selective and functional $NK_3$ antagonists expected to be useful in the treatment of pain, depression, anxiety, panic, schizophrenia, neuralgia, addiction disorders, inflammatory diseases, gastrointestinal disorders, vascular disorders, and neuropathological disorders.

6 Claims, No Drawings

3-ALKYL-3-PHENYL-PIPERIDINES

CROSS REFERENCE TO RELATED APPLICATIONS

This application is a continuation of U.S. Ser. No. 09/467,431 filed Dec. 20, 1999, now abandoned, which is a divisional of U.S. Ser. No. 08/983,584 filed Jan. 22, 1998, now U.S. Pat. No 6,040,316 issued Mar. 21, 2000, which is a 371 filing of PCT/US97/15443 filed Sep. 2, 1997, priority based on Provisional Application No. 60/026,385 filed Sep. 16, 1996.

BACKGROUND OF THE INVENTION

Over the last decade, major advances have been made in the understanding of the biology of the mammalian tachykinin neuropeptides. It is now well established that substance-P (1), neurokinin A (NKA) (2), and neurokinin B (NKB) (3), all of which share a common C-terminal sequence Phe-X-Gly-Leu-Met-NH$_2$. (Nakanishi S., *Physiol. Rev.*, 1987;67:117), are widely distributed throughout the periphery and central nervous system (CNS) where they appear to interact with at least three receptor types referred to as $NK_1$, $NK_2$, and $NK_3$, (Guard S., et al., *Neurosci. Int.*, 1991;18:149). Substance-P displays highest affinity for $NK_1$ receptors, whereas NKA and NKB bind preferentially to $NK_2$ and $NK_3$ receptors, respectively. Recently, all three receptors have been cloned and sequenced and shown to be members of the G-protein-linked "super family" of receptors (Nakanishi S.,*Annu. Rev. Neurosci.*, 1991;14:123). A wealth of evidence supports the involvement of tachykinin neuropeptides in a variety of biological activities including pain transmission, vasodilation, smooth muscle contraction, bronchoconstriction, activation of the immune system (inflammatory pain), and neurogenic inflammation (Pernow B., *Pharmacol. Rev.*, 1983;35:85). However, to date, a detailed understanding of the physiological roles of tachykinin neuropeptides has been severely hampered by a lack of selective, high affinity, metabolically stable tachykinin receptor antagonists that possess both good bioavailability and CNS penetration. Although several tachykinin receptor antagonists have been described (Tomczuk B. E., et al., *Current Opinions in Therapeutic Patents,* 1991;1:197), most have been developed through the modification and/or deletion of one or more of the amino acids that comprise the endogenous mammalian tachykinins such that the resulting molecules are still peptides that possess poor pharmacokinetic properties and limited in vivo activities.

However, since 1991, a number of high-affinity nonpeptide antagonists have been reported. Snider R. M., et al., (*Science,* 1991;251:435), and Garret C., et al., (*Proc. Natl. Acad. Sci.,* 1991;88:10208), described CP-96,345 and RP 67580, respectively, as antagonists at the $NK_1$ receptor, while Advenier C., et al., (*Brit. J. Pharmacol.,* 1992;105:78), presented data on SR 48968 showing its high affinity and selectivity for $NK_2$ receptors. More recently Macleod, et al., (*J. Med. Chem.,* 1993;36:2044) have published on a novel series of tryptophan derivatives as $NK_1$ receptor antagonists. It is of interest that most of the non-peptide tachykinin receptor antagonists described to date arose, either directly or indirectly, out of the screening of large compound collections using a robust radioligand binding assay as the primary screen. Recently, FK 888, a "dipeptide" with high affinity for the $NK_1$ receptor was described (Fujii J., et al., *Neuropeptide,* 1992;22:24). Only one $NK_3$ receptor selective ligand, SR 142801, has been published on to date (Edmonds-Alt, et al., *Life Sciences,* 1995;56:27).

International Publication Numbers WO 93/01169, WO 93/01165, and WO 93/001160 cover certain nonpeptide tachykinin receptor antagonists.

NKB and also $NK_3$ receptors are distributed throughout the periphery and central nervous system (Maggi, et al., *J. Auton. Pharmacol.,* 1993;13:23). NKB is believed to mediate a variety of biological actions via the $NK_3$ receptor including gastric acid secretion; appetite regulation; modulation of serotonergic, cholinergic, and dopaminergic systems; smooth muscle contraction and neuronal excitation. Recent publications descriptive of this art include Polidor, et al., *Neuroscience Letts.,* 1989;103:320; Massi, et al., *Neuroscience Letts.,* 1988;92:341, and Improta, et al., *Peptides,* 1991;12:1433. Due to its actions with dopaminergic (Elliott, et al., *Neuropeptides,* 1991;19:119), cholinergic (Stoessl, et al., *Psycho. Pharmacol.,* 1988;95:502), and serotonergic (Stoessl, et al., *Neuroscience Letts.,* 1987;80:321) systems, NKB may play a role in psychotic behavior, memory functions, and depression.

Accordingly, compounds capable of antagonizing the effects of NKB at $NK_3$ receptors will be useful in treating or preventing a variety of disorders including pain, depression, anxiety, panic, schizophrenia, neuralgia, addiction disorders, inflammatory diseases; gastrointestinal disorders including colitis, Crohn's disease, inflammatory bowel disorder, and satiety; vascular disorders such as angina and migraine and neuropathological disorders such as Parkinsonism and Alzheimer's.

SUMMARY OF THE INVENTION

The instant invention is a compound of formula

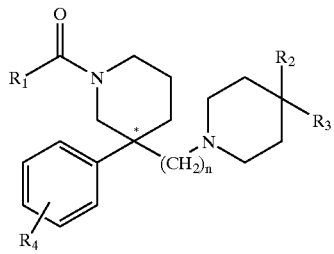

I or a pharmaceutically acceptable salt thereof wherein:

$R_1$ is straight or branched alkyl of from 5 to 15 carbon atoms, aryl, or heteroaryl;

$R_2$ is hydrogen, hydroxy, amino, or thiol;

$R_3$ is aryl, arylsulfonylmethyl, or saturated or unsaturated heterocycle;

$R_4$ is from 1 to 4 groups each independently selected from halogen, alkyl, hydroxy, and alkoxy;

n is an integer of from 2 to 6; and the ($CH_2$) group can be replaced by oxygen, nitrogen, or sulphur.

Preferred compounds of the invention are those of Formula I wherein:

$R_1$ is phenyl, naphthyl, piperidinyl, imidazolyl, or tetrazole;

$R_2$ is hydrogen, hydroxy, or amino;

$R_3$ is phenyl, fluorophenyl, hydroxyphenyl, or phenylsulfonylmethyl;

$R_4$ is dichloro, difluoro, dimethoxy, or dimethyl; and n is an integer of from 2 to 6.

More preferred compounds of the invention are those of Formula I wherein:

$R_1$ is phenyl, naphthyl, piperidinyl, or imidazolyl;
$R_2$ is hydrogen or hydroxy;
$R_3$ is phenyl, 4-fluorophenyl, 4-hydroxyphenyl, or phenylsulfonylmethyl;
$R_4$ is 3,4-dichlorophenyl; and
n is the integer 2 to 4.

Still more preferred compounds of the instant invention are those of Formula I wherein:
$R_1$ is phenyl;
$R_2$ is hydrogen or hydroxy;
$R_3$ is phenylsulfonylmethyl or phenyl;
$R_4$ is 3,4-dichloro; and
n is 3.

The most preferred compounds of the invention are selected from but not limited to:

(R)-{3-(3,4-Dichloro-phenyl)-3-[3-(4-phenyl-piperidin-1-yl)-propyl]-piperidin-1-yl}-phenyl-methanone monohydrochloride;

(S)-{3-(3,4-Dichloro-phenyl)-3-[3-(4-hydroxy-4-phenyl-piperidin-1-yl)-propyl]-piperidin-1-yl}-phenyl-methanone monohydrochloride;

(S)-[3-[3-(4-Benzenesulfonylmethyl-4-hydroxy-piperidin-1-yl)-propyl]-3-(3,4-dichloro-phenyl)-piperidin-1-yl]-phenyl-methanone monohydrochloride;

(R)-{3-(3,4-Dichloro-phenyl)-3-[3-(4-hydroxy-4-phenyl-piperidin-1-yl)-propyl]-piperidin-1-yl}-naphthalene-2-yl-methanone;

(R)-{3-(3,4-Dichloro-phenyl)-3-[3-(4-hydroxy-4-phenyl-piperidin-1-yl)-propyl]-piperidin-1-yl}-pyridin-4-yl-methanone;

N-(1-{3-[3-(3,4-Dichloro-phenyl)-1-(1H-imidazole-2-carbonyl)-piperidin-3-yl]-propyl}-4-phenyl-piperidin-4-yl)-acetamide;

(R)-{3-(3,4-Dichloro-phenyl)-3-[3-(4-hydroxy-4-phenyl-piperidin-1-yl)-propyl]-piperidin-1-yl}-phenyl-methanone;

(R)-{3-(3,4-Dichloro-phenyl)-3-[3-(4-phenyl-piperidin-1-yl)-propyl]-piperidin-1-yl}-phenyl-methanone;

(3-(3,4-Dichloro-phenyl)-3-{3-[4-(4-fluoro-phenyl)-4-hydroxy-piperidin-1-yl]-propyl}-piperidin-1-yl)-phenyl-methanone;

[3-[3-(4-Benzenesulfonylmethyl-4-hydroxy-piperidin-1-yl)propyl]-3-(3,4-dichloro-phenyl)-piperidin-1-yl]-phenyl-methanone;

{3-(4-Fluoro-phenyl)-3-[3-(4-hydroxy-4-phenyl-piperidin-1-yl)-propyl]-piperidin-1-yl}-phenyl-methanone;

{3-(3,4-Dimethoxy-phenyl)-3-[3-(4-hydroxy-4-phenyl-piperidin-1-yl)-propyl]-piperidin-1-yl}-phenyl-methanone;

{3-(3,4-Dimethyl-phenyl)-3-[3-(4-hydroxy-4-phenyl-piperidin-1-yl)-propyl]-piperidin-1-yl}-phenyl-methanone;

[3-[3-(4-Hydroxy-4-phenyl-piperidin-1-yl)-propyl]-3-(3,4,5-trichloro-phenyl)-piperidin-1-yl]-phenyl-methanone;

{3-(3,4-Dichloro-phenyl)-3-[4-(4-hydroxy-4-phenyl-piperidin-1-yl)-butyl]-piperidin-1-yl}-phenyl-methanone;

{3-(3,4-Dichloro-phenyl)-3-[6-(4-hydroxy-4-phenyl-piperidin-1-yl)-hexyl]-piperidin-1-yl}-phenyl-methanone;

[3-{2-[(4-Benzenesulfonylmethyl-4-hydroxy-piperidin-1-ylmethyl)-amino]-ethyl}-3-(3,4-dichloro-phenyl)-piperidin-1-yl]-phenyl-methanone;

[3-{2-[(4-Benzenesulfonylmethyl-4-hydroxy-piperidin-1-ylmethyl)-methyl-amino]-ethyl}-3-(3,4-dichlorophenyl)-piperidin-1-yl]-phenyl-methanone;

[3-[2-(4-Benzenesulfonylmethyl-4-hydroxy-piperidin-1-ylmethoxy)-ethyl]-3-(3,4-dichlorophenyl)-piperidin-1-yl]-phenyl-methanone;

[3-[2-(4-Benzenesulfonylmethyl-4-hydroxy-piperidin-1-ylmethylsulfanyl)-ethyl]-3-(3,4-dichloro-phenyl)-piperidin-1-yl]-phenyl-methanone;

(3-(3,4-Dichloro-phenyl)-3-{2-[(4-hydroxy-4-phenyl-piperidin-1-ylmethyl)-amino]-ethyl}-piperidin-1-yl)-phenyl-methanone;

(3-(3,4-Dichloro-phenyl)-3-{2-[(4-hydroxy-4-phenyl-piperidin-1-ylmethyl)-methyl-amino]-ethyl}-piperidin-1-yl)-phenyl-methanone;

{3-(3,4-Dichloro-phenyl)-3-[2-(4-hydroxy-4-phenyl-piperidin-1-ylmethoxy)-ethyl]-piperidin-1-yl}-phenyl-methanone;

{3-(3,4-Dichloro-phenyl)-3-[2-(4-hydroxy-4-phenyl-piperidin-1-ylmethylsulfanyl)-ethyl]-piperidin-1-yl}-phenyl-methanone;

[3-{[2-(4-Benzenesulfonylmethyl-4-hydroxy-piperidin-1-yl)-ethylamino]-methyl)-3-(3,4-dichloro-phenyl)-piperidin-1-yl]-phenyl-methanone;

[3-[2-(4-Benzenesulfonylmethyl-4-hydroxy-piperidin-1-yl)-ethyl]-methyl-amino}-methyl)-3-(3,4-dichlorophenyl)-piperidin-1-yl]-phenyl-methanone;

[3-[2-(4-Benzenesulfonylmethyl-4-hydroxy-piperidin-1-yl)-ethoxymethyl]-3-(3,4-dichlorophenyl)-piperidin-1-yl]-phenyl-methanone;

[3-[2-(4-Benzenesulfonylmethyl-4-hydroxy-piperidin-1-yl)-ethylsulfanylmethyl]-3-(3,4-dichloro-phenyl)-piperidin-1-yl]-phenyl-methanone;

(3-(3,4-Dichloro-phenyl)-3-{[2-(4-hydroxy-4-phenyl-piperidin-1-yl)-ethylamino]-methyl}-piperidin-1-yl)-phenyl-methanone;

[3-(3,4-Dichloro-phenyl)-3-{[2-(4-hydroxy-4-phenyl-piperidin-1-yl)-ethyl]-methyl-amino}-methyl)-piperidin-1-yl]-phenyl-methanone;

{3-(3,4-Dichloro-phenyl)-3-[2-(4-hydroxy-4-phenyl-piperidin-1-yl)-ethoxymethyl]-piperidin-1-yl}-phenyl-methanone;

{3-(3,4-Dichloro-phenyl)-3-[2-(4-hydroxy-4-phenyl-piperidin-1-yl)-ethylsutfanylmethyl]-piperidin-1-yl}-phenyl-methanone;

[3-[(4-Benzenesulfonylmethyl-4-hydroxy-piperidin-1-ylmethyl)-amino]-3-(3,4 dichloro-phenyl)piperidin-1-yl]-phenyl-methanone;

[3-[2-(4-Benzenesulfonylmethyl-4-hydroxy-piperidin-1-yl)-ethylamino]-3-(3,4-dichlorophenyl)-piperidin-1-yl]-phenyl-methanone;

[3-[3-(4-Benzenesulfonylmethyl-4-hydroxy-piperidin-1-yl)-propylamino]-3-(3,4-dichlorophenyl)-piperidin-1-yl]-phenyl-methanone;

[3-[(4-Benzenesulfonylmethyl-4-hydroxy-piperidin-1-ylmethyl)-methyl-amino]-3-(3,4-dichlorophenyl)-piperidin-1-yl]-phenyl-methanone;

[3-{[2-(4-Benzenesulfonylmethyl-4-hydroxy-piperidin-1-yl)-ethyl]-methyl-amino}-3-(3,4-dichloro-phenyl)-piperidin-1-yl]-phenyl-methanone;

[3-{[3-(4-Benzenesulfonylmethyl-4-hydroxy-piperidin-1-yl)-propyl]-methyl-amino}-3-(3,4-dichloro-phenyl)-piperidin-1-yl]-phenyl-methanone;

[3-(4-Benzenesulfonylmethyl-4-hydroxy-piperidin-1-ylmethoxy)-3-(3,4-dichloro-phenyl)-piperidin-1-yl]-phenyl-methanone;

[3-[2-(4-Benzenesulfonylmethyl-4-hydroxy-piperidin-1-yl)-ethoxy]-3-(3,4-dichlorophenyl)-piperidin-1-yl]-phenyl-methanone;

[3-[3-(4-Benzenesulfonylmethyl-4-hydroxy-piperidin-1-yl)-propoxy]-3-(3,4-dichlorophenyl)-piperidin-1-yl]-phenyl-methanone;

[3-(4-Benzenesulfonylmethyl-4-hydroxy-piperidin-1-ylmethylsulfanyl)-3-(3,4-dichlorophenyl)-piperidin-1-yl]-phenyl-methanone;

[3-[2-(4-Benzenesulfonylmethyl-4-hydroxy-piperidin-1-yl)-ethylsulfanyl]-3-(3,4-dichlorophenyl)-piperidin-1-yl]-phenyl-methanone;

[3-[3-(4-Benzenesulfonylmethyl-4-hydroxy-piperidin-1-yl)-propylsulfanyl]-3-(3,4-dichlorophenyl) piperidin-1-yl]-phenyl-methanone;

{3-(3,4-Dichloro-phenyl)-3-[(4-hydroxy-4-phenyl-piperidin-1-ylmethyl)-amino]-piperidin-1-yl}-phenyl-methanone;

{3-(3,4-Dichloro-phenyl)-3-[2-(4-hydroxy-4-phenyl-piperidin-1-yl)-ethylamino]-piperidin-1-yl}-phenyl-methanone;

{3-(3,4-Dichloro-phenyl)-3-[3-(4-hydroxy-4-phenyl-piperidin-1-yl)-propylamino]-piperidin-1-yl}-phenyl-methanone;

{3-(3,4-Dichloro-phenyl)-3-[(4-hydroxy-4-phenyl-piperidin-1-ylmethyl)-methyl-amino]-piperidin-1-yl}-phenyl-methanone;

(3-(3,4-Dichloro-phenyl)-3-{[2-(4-hydroxy-4-phenyl-piperidin-1-yl)-ethyl]-methyl-amino}-piperidin-1-yl)-phenyl-methanone;

(3-(3,4-Dichloro-phenyl)-3-{[3-(4-hydroxy-4-phenyl-piperidin-1-yl)-propyl]-methyl-amino}-piperidin-1-yl)-phenyl-methanone;

[3-(3,4-Dichloro-phenyl)-3-(4-hydroxy-4-phenyl-piperidin-1-ylmethoxy)-piperidin-1-yl]-phenyl-methanone;

{3-(3,4-Dichloro-phenyl)-3-[2-(4-hydroxy-4-phenyl-piperidin-1-yl)-ethoxy]-piperidin-1-yl}-phenyl-methanone;

{3-(3,4-Dichloro-phenyl)-3-[3-(4-hydroxy-4-phenyl-piperidin-1-yl)-propoxy]-piperidin-1-yl}-phenyl-methanone;

[3-(3,4-Dichloro-phenyl)-3-(4-hydroxy-4-phenyl-piperidin-1-ylmethylsulfanyl)-piperidin-1-yl]-phenyl-methanone;

{3-(3,4-Dichloro-phenyl)-3-[2-(4-hydroxy-4-phenyl-piperidin-1-yl)-ethylsulfanyl]-piperidin-1-yl}-phenyl-methanone; and {3-(3,4-Dichloro-phenyl)-3-[3-(4-hydroxy-4-phenyl-piperidin-1-yl)-propylsulfanyl]-piperidin-1-yl}-phenyl-methanone.

Another aspect of the invention is a pharmaceutical composition containing one or more compound of Formula I above in a therapeutically effective amount together with a pharmaceutically acceptable carrier The compounds of the invention are useful in the treatment of central nervous system disorders such as anxiety, emesis, depression, psychoses, and schizophrenia. They are also useful in the treatment of inflammatory disease, pain, migraine, asthma, and emesis. They are also useful in the treatment of Alzheimer's disease and Parkinsonism.

DETAILED DESCRIPTION

The compounds of the instant invention are selective tachykinin $NK_3$ receptor antagonists. These are small compounds which have the advantage of good bioavailability.

The compounds of Formula I are as described above.

The term "alkyl" is a straight, branched, or unsaturated group of from 5 to 15 carbon atoms such as n-pentyl, n-hexyl, 2,2-dimethyldodecyl, isopentyl, n-heptyl, n-octyl, n-nonyl, undecyl, dodecyl, 3,4-alkene, 2-tetradecyl, and the like unless otherwise stated.

The term "aryl" is a phenyl, or naphthyl group which may be unsubstituted or substituted with from 1 to 4 groups each independently selected from halogen, alkyl, alkoxyl, and hydroxy.

The term "heteroaryl" (or heterocycle) includes compounds containing nitrogen, oxygen, and/or sulfur. Such groups include but are not limited to pyridinyl pyrazole, isoxazole, imidazole, furan, thiophene, pyrrole, tetrazole, and thiazole. Each group may be unsubstituted or substituted with from 1 to 4 groups each independently selected from halogen, alkyl, alkoxyl, and hydroxy.

The term "arylsulfonylmethyl" is as described above for aryl with a sulfonylmethyl attached. Such groups as subtituted phenyl or hetroaryl are examples.

The term "halogen" is fluorine, chlorine, bromine, and iodine. The preferred halogens are chlorine and fluorine.

The term amino refers to unsubstituted mono- or disubstituted groups. The substituents are as described for alkyl above. Preferred substituents are methyl and ethyl.

The compounds of this invention are selective $NK_3$ antagonists. Their activities can be demonstrated by the following assays.

1. Receptor Binding in Transfected CHO Cells

CHO cells expressing either human $NK_1$ or $NK_3$ receptors were cultured in Ham's F-12 Nutrient Mixture supplemented with 10% fetal call serum and 1% penicillin/streptomycin. Cells were seeded to 96-well Wallac (Gaithersburg, Md.) rigid crosstalk corrected cell culture plate 1 day before experiment. On the day of each experiment, cells were washed twice with phosphate buffered saline (PBS) and appropriate agonists or antagonists were added and incubated in 0.2 nM $^{125}$I-labeled ligand in PBS containing 0.4 mg/mL BSA, 0.08 mg/mL bacitracin, 0.004 mg/mL chymostatin, 0.004 mg/mL leupeptin, 1 $\mu$M thiorphan, 25 $\mu$M phosphoramidon, and 2 mM $MnCl_2$. The cells were incubated for 1 hour at room temperature and the reactions terminated by two washes with ice cold PBS. Fifty microliters of 2% SDS followed by 175 $\mu$L of Ready Gel (Beckman) were added to each well. Plates were vortexed, and the radioactivity was quantified in a Wallac 1450 microbeta scintillation counter. Nonspecific binding was determined in the presence of 1 $\mu$M unlabeled corresponding ligand. Receptor binding data were analyzed with nonlinear curve fitting using KaleidaGraph software package (PCS Inc., Reading, Pa.). $IC_{50}$ values were determined using a modified Hill equation, $$\% \text{ Inhibition} = \frac{cpm(L) - cpm(1 \text{ μM cold ligand})}{cpm(0) - cpm(1 \text{ μM cold ligand})} = \frac{L^n}{IC_{50}^n + L^n},$$

where cold ligand represents unlabeled ligand, L represents the concentration of unlabeled ligand, n the Hill coefficient, and $IC_{50}$ the concentration of unlabeled ligand that causes 50% inhibition of the total specific binding of 0.2 nM radiolabeled ligand.

The compounds as exemplified in Table 1 have been shown to displace radioligand for the $NK_3$ receptor at a concentration range of 6 to 18 nM, whereas their affinities for the $NK_1$ receptor are much lower. Detailed data is provided in Table 1.

TABLE 1

| Compounds (See Scheme 3) | $IC_{50}$ (nM) Binding to Human $NK_3$ Receptors | Binding to Human $NK_1$ Receptors |
|---|---|---|
| 20-3 | 17.8 ± 1.5 | 694 ± 89 |
| 20-1 | 5.9 ± 0.4 | >1000 |
| 20-2 | 6.2 ± 0.6 | >1000 |

2. Inhibition of Phosphatidylinositol Turnover in Transfected CHO Cells

The inhibitory effects of these compounds on agonist-induced phosphatidylinositol turnover was estimated by measuring their effects on inositol phosphates (IP) accumulation in CHO cells expressing $NK_3$ receptors. Briefly, cells (10,000/well) were seeded in 96-well cell culture plates 24 hours before changing medium to EMEM/F-12 (w/Earle's salt, w/glutamine; GIBCOL) containing 10 μCi/mL [$^3$H] inositol. After overnight incubation with [$^3$H]inositol, medium was removed and cells were washed twice with assay buffer (MEM with 10 mM LiCl, 20 mM HEPES, and 1 mg/mL BSA). Cells were then incubated with various concentrations of agonists with or without 1 μM of tested compounds for 1 hour. Reactions were stopped by two washes with ice-cold PBS followed by the addition of 0.1 mL ice-cold 5% TCA to each well. The TCA extract was applied to a cation exchange column containing AG 1-X8 resin (Bio-Rad) and washed three times with 5 mM myo-inositol. Inositol phosphates (IP) was eluted with 1 M ammonium formate/0.1 M formic acid. Radioactivity was determined by liquid scintillation counting. Data were analyzed with nonlinear curve fitting using KaleidaGraph software package (PCS Inc, Reading, Pa.). The pKB values in Table 2 were calculated according to the formula: pKB=log (dose ratio−1)−log[B].

TABLE 2

| Compounds | pKB |
|---|---|
| 20-3 | 7.9 ± 0.3 |
| 20-1 | 8.2 ± 0.4 |
| 20-2 | 8.3 ± 0.5 |

In conclusion, data presented in Table 1 (binding assay) and in Table 2 (functionial assay) demonstrate that the compounds of the invention are potent and selective antagonists for the human tachykinin $NK_3$ receptor.

TABLE 3

Mean (SD) Pharmacokinetic Parameters of NK3 Receptor Antagonists in Male Wistar Rats Receiving an Oral Dose of ~20 mg/kg

| Compounds | N | tmax (hr) | Cmax (ng/mL) | t½ (hr) | AUC(0–tldc) (ng · hr/mL) | F (%) |
|---|---|---|---|---|---|---|
| 20-2 | 3 | 1.3 (0.6) | 125.4 (8.0) | 7.4 (1.3) | 716 (56) | — |
| 20-3 | 3 | 1.8 (1.9) | 107 (44) | — | 572 (174) | — |
| 20-1 | 3 | 1.3 (0.6) | 74.0 (12.9) | — | 366 (140) | — |
| SR 142801[a] | 3 | 1.8 (1.9) | 133 (49) | 5.3 (1.5) | 703 (213) | — |

All compounds Were Administered as a Solution in PEG 400/Ethanol/Water (40/15/45)
tmax = Time to reach the highest plasma concentration.
Cmax = The highest plasma concentration.
t½ = Terminal elimination half-life.
AUC(0–tldc) = Area under the plasma concentration-time curve from zero time to the last detectable concentration.
% F = Absolute oral bioavailability calculated as the ratio of oral AUC to intravenous AUC with dose normalization.
[a]Sanofi compound The compounds of the invention are equal to the reference standard in the pharmacokinetic parameters studied. This indicates that compounds of this type will provide desirable pharmaceuticals with bioavailability.

General Procedure for Preparing Intermediate and Final Products of the Invention The synthesis of intermediate (A) is shown in Scheme I below. The reaction of 3-bromopropanol (1) with dihydropyran and catalytic amount of p-toluenesulfonic acid gave quantitative yield of THP protected alcohol (2). Deprotonation of 3,4-dichlorophenylacetonitrile (3) with NaH in THF at room temperature followed by the addition of (2) to the mixture gave the alkylation product (4) in 82% yield. A second alkylation of (4) using KHMDS as base at −78° C. in THF, and ethyl 3-bromopropionate gave ester (5) in 94% yield. Catalytic hydrogenation with Raney Ni and $NH_4OH$, in ethanol for 2 days, reduced the cyano group of (5) to amine, which then cyclized with the ester to give lactam (6) in 85% yield. Reduction of the piperidone (6) with LAH gave the corresponding piperidine (7). The THP group was removed by HCl in dry ether, and the resulting racemic hydroxy piperidine (8) was resolved with (S)-(+)-camphorsulfonic acid in iPrOH to give the diastereomeric salt, with >94% ee of (R)-(+)-(9) in 32% yield. The (R)-(+)-(9) salt was then treated with PhCOCl and $iPr_2NEt$ in $CH_2Cl_2$ to give N-benzoyl amide (10) in 90% yield. The primary hydroxy group of (10) was then converted to iodide by mesylation, and iodization, to give intermediate (A).

The synthesis of intermediate (B) is shown in Scheme II below, started from piperidone hydrate hydrochloride and methylphenylsulfone in the presence of n-BuLi after piperidone was protected by BOC group, and then the BOC protection was removed by TFA solution to obtain Compound B-2. The N-benzyl-4-hydroxy-4-phenyl piperidine was hydrogenated to give B-3.

The coupling of iodide (A) and substituted piperidine (B)-HCl was performed with $KHCO_3$ in MeCN at 60° C. for 20 hours to give the expected product. See Scheme III below.

EXPERIMENTS 2-(3,4-Dichloro-phenyl)-5-(tetrahydro-pyran-4-yloxy)-pentanenitrile (4)

To a suspension of NaH (7.6 g, 0.191 mol) in THF (90 mL) was added slowly a solution of 3,4-dichlorophenylacetonitrile (32.3 g, 0.174 mol) in dry THF (40 mL). The mixture was stirred at room temperature for 2 hours, then cooled in dry ice-acetone bath. A solution of THP protected 3-bromopropanol (42.6 g, 0.191 mol, 1.1 eq) in dry THF (50 mL) was added dropwise to this solution. After the addition was completed, the reaction was warmed to room temperature and stirred at room temperature overnight (20 hours). The reaction was then quenched with saturated NH$_4$Cl solution (ca. 5 mL) and ether (300 mL) was added. The organic phase was then washed with saturated NaHCO$_3$, brine, and dried (MgSO$_4$). After filtration, solvent was removed, and the crude oil was purified by flash column chromatography (Hexane-AcOEt/8:1). The product weight 46.8 g (82.2%) as light yellow oil.

4-Cyano-4-(3,4-dichlorophenyl)-7-(tetrahydropyran-4-yloxy)-heptanoic Acid Ethyl Ester (5)

Potassium hexamethyldisilazide (0.5 M in toluene, 285 mL, 0.143 mol) was added dropwise to a solution of (4) (39 g, 0.119 mol) in THF (240 mL) under nitrogen and stirred at room temperature for 1 hour. A solution of ethyl 3-bromopropionate (22.8 mL, 0.178 mol, 1.5 eq) in THF (45 mL) was added to the reaction mixture all at once. After stirring at room temperature for 4 hours, the reaction was quenched with saturated NH$_4$Cl solution (20 mL). The organic solution was dried over MgSO$_4$, and solvent is evaporated. The crude oil was purified by flashed chromatography (hexane-AcOEt/8:1) to give light yellow oil (48.03 g, 94.4% yield).

5-(3,4-Dichlorophenyl)-5-[3-(tetrahydropyran-4-yloxy)-propyl]-2-piperidone (6)

Raney Ni is added to a solution of cyanoester (5) (8.5 g, 19.84 mmol) in absolute EtOH (200 mL) and concentrated NH$_4$OH (40 mL), The mixture was subjected to a H$_2$ (51.8 psi) Par for 64.5 hours. The reaction mixture was filtered through celite, and N$_2$ gas was passed through the solution to remove NH$_3$. EtOH was then evaporated, and water is azeotropically removed with toluene. The crude oil is purified by flash chromatography (Ch$_2$Cl$_2$—MeOH/95:5) to give a colorless solid (6.5 g, 84.8% yield), mp ~45° C.

3-(3,4-Dichlorophenyl)-3-[3-(tetrahydropyran-4-yloxy)-propyl]-piperidine (7)

Piperidone (6) (42.9 g, 0.111 mol) in dry THF (300 mL) was added to a suspension of LAH (8.4 g, 0.222 mol) in dry THF (500 mL), which was then heated under N$_2$ at 60° C. in an oil bath for 5 hours, then cooled and stirred at room temperature overnight (20 hours). The reaction was quenched by H$_2$O (8.5 mL), 4N NaOH (8.5 mL), and H$_2$O (0.5 mL), respectively. White solid was filtered and washed with Et$_2$O. The filtrate was concentrated, and the crude oil was purified by flash chromatography (CH$_2$Cl$_2$—MeOH/95:5) to give a colorless oil (37.94 g 91.8%).

3-[3-(3,4-Dichlorophenyl)-piperidin-3-yl]-propan-1-ol (8)

A solution of dry HCl.OEt$_2$ was added to a solution of piperidine (7) (20.2 g, 54.36 mmol) in MeOH (200 mL) until pH ~1. The mixture was stirred at room temperature for 30 minutes. Solvent was evaporated, the residue was dissolved in CH$_2$Cl$_2$ (300 mL) and stirred with 1N NaOH (100 mL) for 15 minutes. The solvent was separated, washed with NaHCO$_3$, and dried over MaSO$_4$. The crude oil was purified by flash chromatography (CH$_2$Cl$_2$—MeOH(saturated with NH$_3$)/95:5) to give a white solid (13.25 g, 84.6%).

(R)-3-[3-(3,4-Dichlorophenyl)-piperidin-3-yl]-propan-1-ol (1s)-7,7-dimethyl-2-oxobicyclo[2.2.1]heptane-1-methanesulfonate (1:1) Salt (9)

A solution of (S)-(+)-camphorsulfonic acid (10.3 g, 44.41 mmol) in iPrOH (10 mL) was added to a solution of hydroxy piperidine (8) (12.8 g, 44.41 mmol) in iPrOH. The mixture was heated to reflux for 15 minutes. The solvent was removed to give glassy solid 23.4 g, which solid was then recrystallized in iPrOH two times to give white crystals (5.5 g, 23.8%, 95% ee), mp 188–189° C.

[3-(3,4-Dichlorophenyl)-3-(3-hydroxy-propyl)-piperidin-1-yl]-phenyl-methanone (10)

Diisopropylethylamine (5.7 mL, 3.27 mmol, 5.0 eq) was added to a mixture of camphorsulfonate salt (9) (3.4 g, 6.53 mmol) in CH$_2$Cl$_2$ (21 mL, 0.3 M) and followed by dropwise addition of PhCOCl (0.83 mL, 7.19 mmol, 1.1 eq). The solution was stirred at room temperature for 1 hour. The reacting mixture was diluted with CH$_2$Cl$_2$ (200 mL) and washed with brine, 1 M KHSO$_4$, and saturated NaHCO$_3$ then dried over MgSO$_4$. The concentrated crude oil was purified by flash chromatography (CH$_2$Cl$_2$—MeOH/95:5) to give white solid (2.30 g, 89.8%).

(R)-Methanesulfonic acid 3-[1-benzoyl-3-(3,4-dichlorophenyl)-piperidin-3-yl]-propyl Ester (11)

Diisopropylethylamine (1.6 mL, 9.18 mmol) was added to a solution of alcohol (10) (1.2 g, 3.06 mmol 3.0 eq) in CH$_2$Cl$_2$ (30 mL) followed by MsCl (0.28 mL, 3.67 mmol, 1.2 eq). The solution was stirred at room temperature for 2 hours, then quenched with water and diluted with CH$_2$Cl$_2$ (200 mL). The organic layer was washed with brine, 1N HCl, saturated NaHCO$_3$, and dried over MgSO$_4$. The crude oil was purified by flash chromatography (CH$_2$Cl$_2$—MeOH/95:5) to give light yellow solid (1.43 g, 99.3%).

(R)-[3-(3,4-Dichlorophenyl)-3-(3-iodopropyl)-piperidin-1-yl]-phenyl-methanone (A)

A solution of KI (2.6 g, 15.43 mmol, 1.1 eq) in acetone (10 mL) was added to a solution of mesylate (11) (6.6 g, 14.03 mmol) in dry acetone (80 mL) plus a drop of Hg. The mixture was heated at reflux (70° C. oil bath) for 18 hours and white solid formed. Acetone was evaporated, the remaining solid was extracted with CH$_2$Cl$_2$. The combined CH$_2$Cl$_2$ extracts were washed with brine, then dried over MgSO$_4$. The crude oil was purified by flash chromatography (hexane-EtOAc/2:1) to give a colorless oil, which solidified after dried at 45° C., 20 mm Hg overnight. The solid weight 6.93 g (98.4%), mp 118–120° C.

{3-[3-(4-Benzensulfonylmethyl-4-hydroxy-piperidin-1-yl]-3-(3,4-dichlorophenyl)-piperidin-1-yl}-phenyl-methanone monohydrochloride (20-1)

A mixture of TFA salt (B-1) (0.26 g, 0.72 mmol), iodide (0.3 g, 0.60 mmol), and KHCO$_3$ (0.3 g, 2.99 mmol) in CH$_3$CN (10 mL) was heated at 60° C. oil bath for 18 hours, under nitrogen atmosphere. Solvent was evaporated, the remaining was dissolved in CH$_2$Cl$_2$ (100 mL). The organic solution was washed with saturated NaHCO$_3$, and dried over Na$_2$SO$_4$. Crude oil was purified by flash chromatography (CH$_2$Cl$_2$—MeOH/95:5) to give white solid, 0.31 g (83%). This solid free base was treated with HCl in ether to give off-white solid 0.3 g as HCl salt, mp 154° C. (dec.).

{3-(3,4-Dichlorophenyl)-3-[3-(4-hydroxy-4-phenyl-piperidin-1-yl)-propyl]-piperidin-1-yl}-phenyl-methanone monohydrochloride (20-2)

This compound was prepared in the same manner for the title compound (20-1), except that compound (B-1) was replaced with compound (B-2), 99% yield, mp 136–140° C.

{3-(3,4-Dichlorophenyl)-3-[3-(4-phenyl-piperidin-1-yl)-propyl]-piperidin-1-yl}-phenyl-methanone monohydrochloride (20-3)

This compound was prepared in the same manner for the title compound (20-1), except that compound (B-1) was replaced with compound (B-3), 94% yield, mp 136–138° C.

4-Benzensulfonylmethyl-4-hydroxy-piperidine TFA (B-1)

Diisopropylethylamine (28.3 mL, 162.75 mmol) and di-t-butyl dicarbonate (28.4 g, 130.02 mmol) were added in sequence to a mixture of piperidone hydrate hydrochloride (12) (10.0 g, 65.1 mmol) in methanol (50 mL). The mixture was stirred at room temperature for 20 hours. The solvent was removed, and the remaining was partitioned in ether and 1 M KHSO$_4$ solution. The organic layer was washed with brine and saturated NaHCO$_3$. The n-BuLi product was purified by flash chromatography to give a white solid (13) (12.0 g, 93%). n-BuLi (6.3 mL, 10.05 mmol, 1.6 M solution in hexane) was added to a solution of methylphenylsulfone (1.6 g, 10.0 mol) in THF (33 mL) at −40° C. After stirring at this temperature for 30 minutes, a solution of N-BOC-piperidone (13)(2.2 g, 11.0 mmol) in dry THF (20 mL) was added to the mixture, stirred at −40° C. for an additional hour and room temperature for another 2 hours. The reaction was worked up and the product was isolated by chromatography (CH$_2$Cl$_2$—MeOH/96.4) to give a solid (14) (3.3 g, 92%). Compound (14) was treated with 5 mL of 50% TFA in dichloromethane for 15 minutes: after the solvent was removed, the pure target compound weight 0.95 g (92%), mp 170–171° C.

4-Phenyl Piperidine HCl (B-3)

A mixture of 4-hydroxy-4-phenylpiperidine (B-2) (39.7 g, 0.224 mol) and Pd/C (4.0 g) and concentrated HCl (20 mL) was subjected to hydrogenation H$_2$ (50 psi) for 20 hours at 40° C. The solid was filtered through celite, and the filtrate was concentrated. A white solid was obtained by recrystallizaiton from ethanol-ether (36.3 g, 82%), mp 170–173° C.

The following were prepared by the methods described above:

- (R)-{3-(3,4-Dichloro-phenyl)-3-[3-(4-phenyl-piperidin-1-yl)-propyl]-piperidin-1-yl}-phenyl-methanone monohydrochloride;
- (S)-{3-(3,4-Dichloro-phenyl)-3-[3-(4-hydroxy-4-phenyl-piperidin-1-yl)-propyl]-piperidin-1-yl}-phenyl-methanone monohydrochloride;
- (S)-[3-[3-(4-Benzenesulfonylmethyl-4-hydroxy-piperidin-1-yl)-propyl]-3-(3,4-dichloro-phenyl)-piperidin-1-yl]-phenyl-methanone monohydrochloride;
- (R)-{3-(3,4-Dichloro-phenyl)-3-[3-(4-hydroxy-4-phenyl-piperidin-1-yl)-propyl]-piperidin-1-yl}-naphthalene-2-yl-methanone;
- (R)-{3-(3,4-Dichloro-phenyl)-3-[3-(4-hydroxy-4-phenyl-piperidin-1-yl)-propyl]-piperidin-1-yl}-pyridin-4-yl-methanone;
- N-(1-{3-[3-(3,4-Dichloro-phenyl)-1-(1H-imidazole-2-carbonyl)-piperidin-3-yl]-propyl}-4-phenyl-piperidin-4-yl)-acetamide;
- (R)-{3-(3,4-Dichloro-phenyl)-3-[3-(4-hydroxy-4-phenyl-piperidin-1-yl)-propyl]-piperidin-1-yl}-phenyl-methanone;
- (R)-{3-(3,4-Dichloro-phenyl)-3-[3-(4-phenyl-piperidin-1-yl)-propyl]-piperidin-1-yl}-phenyl-methanone;
- (3-(3,4-Dichloro-phenyl)-3-{3-[4-(4-fluoro-phenyl)-4-hydroxy-piperidin-1-yl]-propyl}-piperidin-1-yl)-phenyl-methanone;
- [3-[3-($^4$-Benzenesulfonylmethyl-4-hydroxy-piperidin-1-yl)propyl]-3-(3,4-dichloro-phenyl)-piperidin-1-yl]-phenyl-methanone;
- {3-(4-Fluoro-phenyl)-3-[3-(4-hydroxy-4-phenyl-piperidin-1-yl)-propyl]-piperidin-1-yl}-phenyl-methanone;
- {3-(3,4-Dimethoxy-phenyl)-3-[3-(4-hydroxy-4-phenyl-piperidin-1-yl)-propyl]-piperidin-1-yl}-phenyl-methanone;
- {3-(3,4-Dimethyl-phenyl)-3-[3-(4-hydroxy-4-phenyl-piperidin-1-yl)-propyl]-piperidin-1-yl}-phenyl-methanone;
- [3-[3-($^4$-Hydroxy-4-phenyl-piperidin-1-yl)-propyl]-3-(3,4,5-trichloro-phenyl)-piperidin-1-yl]-phenyl-methanone;
- {3-(3,4-Dichloro-phenyl)-3-[4-(4-hydroxy-4-phenyl-piperidin-1-yl)-butyl]-piperidin-1-yl}-phenyl-methanone; and
- {3-(3,4-Dichloro-phenyl)-3-[6-(4-hydroxy-4-phenyl-piperidin-1-yl)-hexyl]-piperidin-1-yl}-phenyl-methanone.

SCHEME I
Synthesis of Intermediate (A)

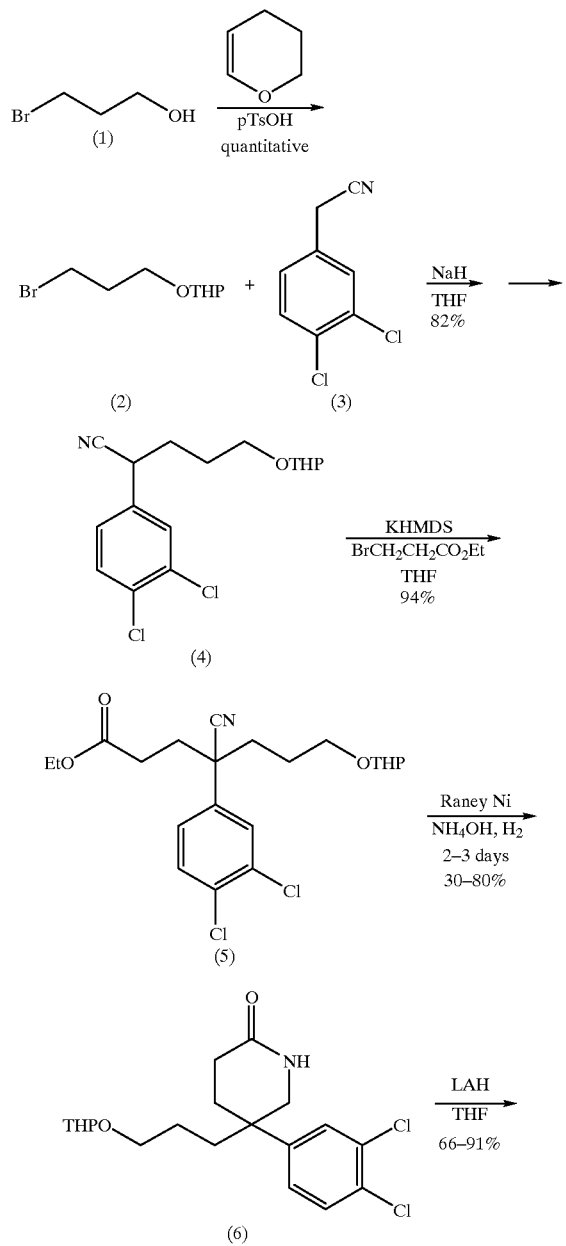

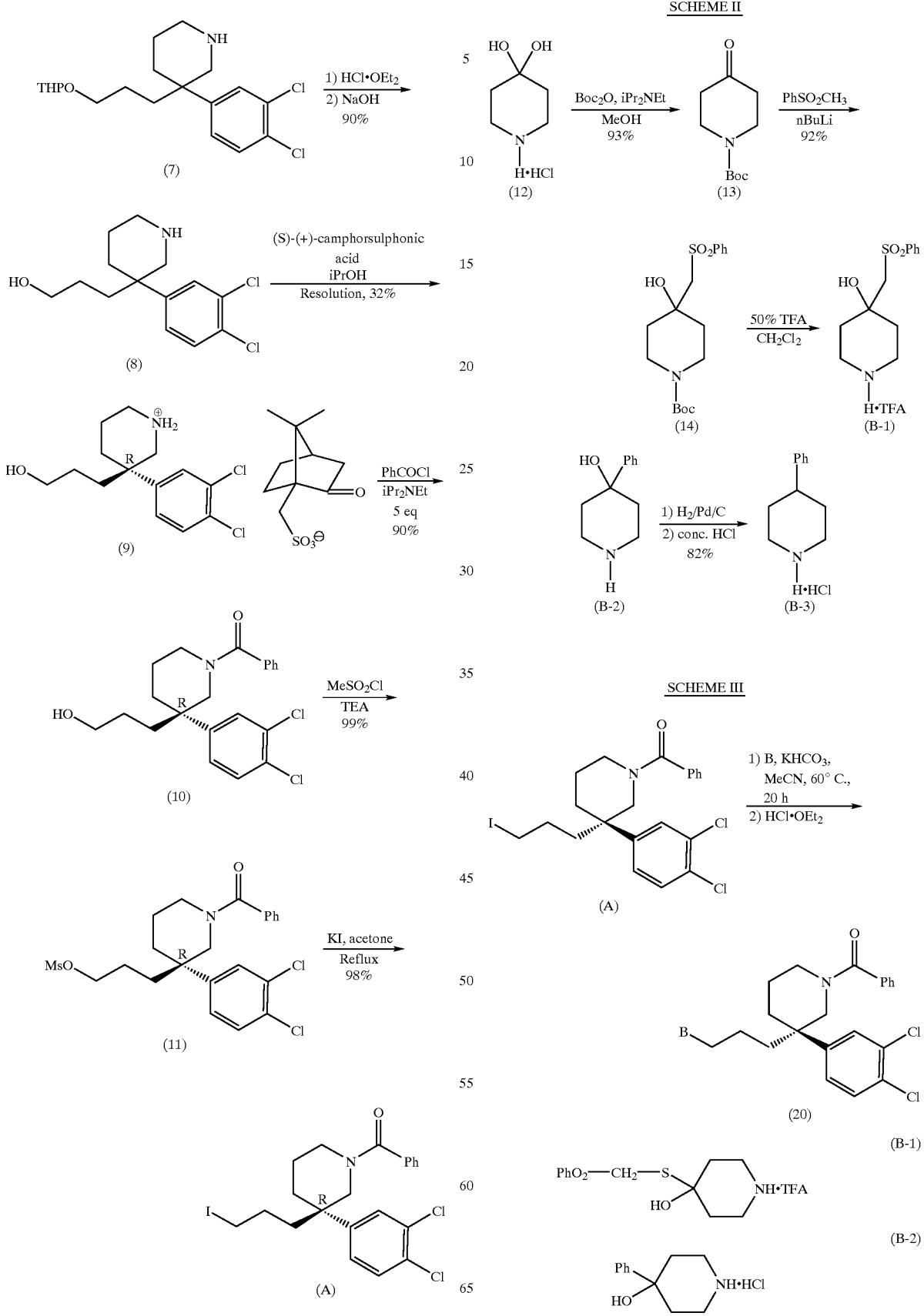

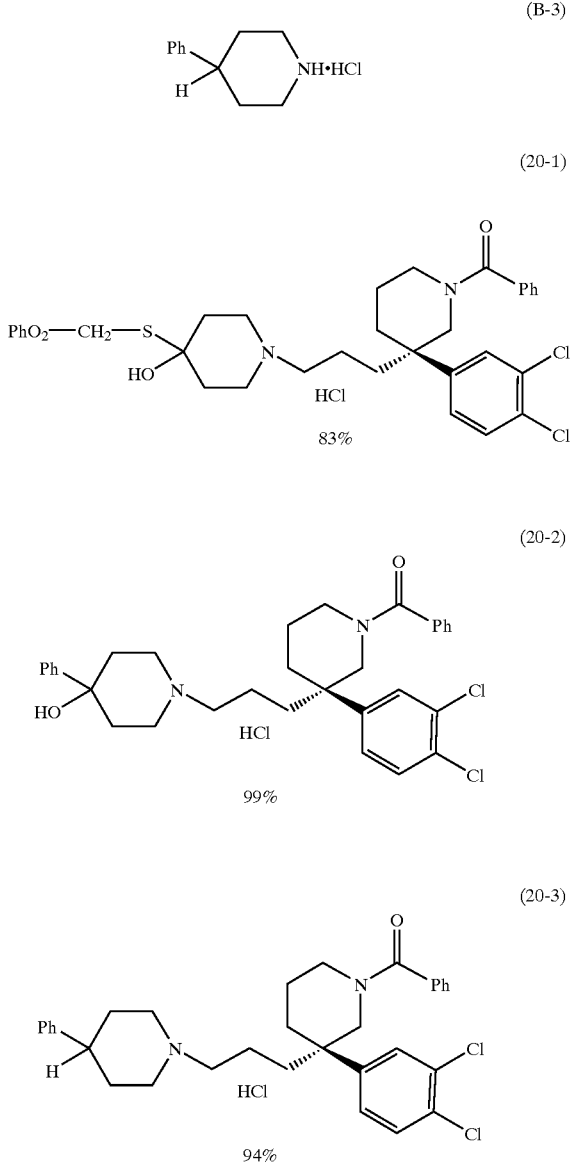

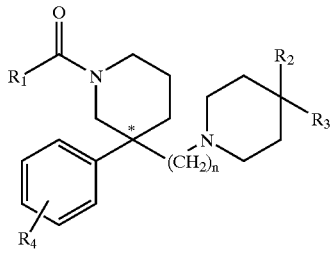

What is claimed is:

1. A compound of formula or a pharmaceutically acceptable salt thereof wherein:
$R_1$ is straight or branched alkyl of from 5 to 15 carbon atoms, aryl, or heteroaryl;
$R_2$ is hydroxy, amino, or thiol group;
$R_3$ is aryl;
$R_4$ is from 1 to 4 groups each independently selected from halogen, alkyl, hydroxy, and alkoxy; and
n is an integer of from 2 to 6; and a carbon atom of $(CH_2)_n$ group can be replaced by oxygen, nitrogen, or sulphur.

2. A compound according to claim 1 wherein:
$R_1$ is phenyl, naphthyl, pyridinyl, imidazolyl, or tetrazolyl;
$R_2$ is hydroxy;
$R_3$ is naphthyl;
$R_4$ is dichloro, difluoro, dimethoxy, or dimethyl; and
n is an integer of from 2 to 6.

3. A compound according to claim 1 wherein:
$R_1$ is phenyl, naphthyl, pypridinyl, or imidazolyl;
$R_2$ is hydroxy;
$R_3$ is naphthyl;
$R_4$ is 3,4-dichloro; and
n is the integer 2 to 4.

4. A compound according to claim 1 wherein:
$R_1$ is phenyl;
$R_2$ is hydroxy;
$R_3$ is naphthyl;
$R_4$ is 3,4-dichloro; and
n is 3.

5. A compound according to claim 1 selected from:
(R)-{3-(3,4-Dichlorophenyl)-3-[3-(4-hydroxy-4-phenyl-piperidin-1-yl)-propyl]-piperidin-1-yl}-naphthalene-2-yl-phenyl-methanone.

6. A pharmaceutical composition comprising a therapeutically effective amount of a compound according to claim 1 and a pharmaceutically acceptable carrier.

* * * * *